United States Patent [19]

Weitz et al.

[11] 4,361,710

[45] Nov. 30, 1982

[54] PREPARATION OF BUTANE-1,4-DIOL

[75] Inventors: Hans-Martin Weitz, Bad Durkheim; Rolf Schnabel, Schifferstadt; Rolf Platz, Mannheim, all of Fed. Rep. of Germany

[73] Assignee: BASF Aktiengesellschaft, Fed. Rep. of Germany

[21] Appl. No.: 347,580

[22] Filed: Feb. 10, 1982

[30] Foreign Application Priority Data

Feb. 24, 1981 [DE] Fed. Rep. of Germany ....... 3106819

[51] Int. Cl.$^3$ ..................... C07C 29/136; C07C 69/60
[52] U.S. Cl. ..................................... 568/864; 560/201
[58] Field of Search ......................... 568/864; 560/201

[56] References Cited

U.S. PATENT DOCUMENTS

| | | | |
|---|---|---|---|
| 3,344,196 | 9/1967 | Corr et al. | 568/864 |
| 3,524,892 | 8/1970 | Horlenko et al. | 568/864 |
| 3,830,830 | 8/1974 | Cleveland et al. | 568/864 |

Primary Examiner—Joseph E. Evans
Attorney, Agent, or Firm—Keil & Witherspoon

[57] ABSTRACT

A process for the preparation of butane-1,4-diol by catalytic hydrogenation of a mixture obtained by treating maleic anhydride with an aliphatic alcohol at elevated temperatures, wherein a monohydric or dihydric aliphatic alcohol of boiling point above 180° C. is used and the mixture of maleic acid and the alcohol is obtained by washing a gaseous reaction mixture, which contains maleic anhydride and is obtained in the catalytic oxidation of hydrocarbons by air, with the alcohol.

4 Claims, No Drawings

PREPARATION OF BUTANE-1,4-DIOL

The present invention relates to a process for the preparation of butane-1,4-diol by catalytic hydrogenation of maleic anhydride in the presence of an alcohol.

Butane-1,4-diol and tetrahydrofuran are known to be useful intermediates, for example for the preparation of polyurethanes, polybutylene terephthalate or polytetrahydrofuran.

Several routes for the large-scale industrial production of butane-1,4-diol and tetrahydrofuran have been described. The greater part of the butane-1,4-diol and tetrahydrofuran produced in industry is obtained via butynediol, which is produced from acetylene and formaldehyde by the Reppe synthesis. However, the recently sharply increasing price of acetylene adversely affects the economics of this synthesis route. Using another, recently developed process, butadienes are acetoxylated, and the butenediol diacetates produced as intermediates are converted into butane-1,4-diol by catalytic hydrogenation followed by hydrolysis. Tetrahydrofuran can be obtained in a conventional manner by cyclization of the butanediol or of the butanediol diacetate produced as an intermediate.

The preparation of butane-1,4-diol by catalytic hydrogenation of maleic anhydride has also been proposed. According to the process described in German Laid-Open Application DOS No. 2,543,673, a mixture obtained by treating maleic anhydride with an aliphatic alcohol at elevated temperatures is hydrogenated to give butane-1,4-diol, which is formed by hydrogenolysis of the but-2-enedicarboxylic acid alkyl ester present in the mixture, and the alcohol used is recovered. German Laid-Open Application DOS No. 2,845,905 discloses that butane-1,4-diol is also obtained when a solution of maleic anhydride in an aliphatic alcohol is hydrogenated, in one stage, at from 180° to 300° C. and under a pressure of from 250 to 350 bar, over a copper chromite catalyst. Monohydric aliphatic alcohols of 1 to 6 carbon atoms are used for these processes.

Since the isolation of maleic anhydride from the reaction gases formed in the oxidation of hydrocarbons, for example benzene, butenes or butane, by air presents substantial technical difficulties, and problems of corrosion arise in the hydrogenation of maleic anhydride, owing to the formation of water and therefore of free maleic acid and succinic acid, the economics of these processes are poor.

We have found that butane-1,4-diol can be prepared substantially more advantageously by catalytic hydrogenation of a mixture obtained by treating maleic anhydride with an aliphatic alcohol at elevated temperatures, when a monohydric or dihydric aliphatic alcohol of boiling point above 180° C. is used and the mixture of maleic acid and the alcohol is obtained by washing a gaseous reaction mixture, which contains maleic anhydride and is obtained in the catalytic oxidation of hydrocarbons by air, with the alcohol.

In the novel process, monohydric or dihydric aliphatic alcohols of boiling points above 180° C. are used, for example monohydric alcohols of not less than 8 carbon atoms, eg. 2-ethylhexanol and dodecan-1-ol, preferred alcohols having boiling points which are not less than 10° C. higher than the boiling point of butane-1,4-diol. Butane-1,4-diol is preferably used as a dihydric alcohol.

The mixture, to be hydrogenated, of maleic anhydride and the alcohol is obtained by washing a gaseous reaction mixture which contains maleic anhydride and is obtained by the conventional catalytic oxidation of hydrocarbons, for example benzene, butenes or butane, by air. In this conventional oxidation process, the gaseous reaction mixture flowing from the reactor is at from 250° to 600° C. and contains, per m$^3$ (S.T.P.), up to 40 g of maleic anhydride. In addition to unreacted hydrocarbons, the gaseous reaction mixture also contains water, carbon monoxide and carbon dioxide.

To absorb the maleic anhydride, the reaction gas containing it is passed, for example, into a column into which the alcohol is introduced at the same time. The alcohol is advantageously employed in excess, ie. in more than twice the molar amount, based on 1 mole of maleic anhydride. From 2.5 to 25 times the molar amount of a monohydric alcohol, and from 5 to 25 times the molar amount of a dihydric alcohol, are preferably used, based on the maleic anhydride. The wash column is advantageously operated at from 120° to 160° C. and below the boiling point of the alcohol used. The absorption is carried out in co-current or in counter-current. The maleic anhydride is washed out from the gaseous reaction mixture by the alcohol, and the half-esters of maleic acid and fumaric acid are predominantly formed. Any alcohol which passes into the gas phase is recovered from the exit gas of the wash column.

The solution of the maleic acid half-ester in the alcohol, which is obtained in the wash column, is heated to 120°-150° C., water being removed at the same time, and the corresponding diesters are formed. If butane-1,4-diol is used as the alcohol, the water of reaction is advantageously removed by distillation.

The diester is finally subjected to catalytic hydrogenation in a conventional manner, at from 180° to 220° C. and under a pressure of from 180 to 400 bar, using a conventional hydrogenation catalyst, for example one of those described in Report 96A of the Stanford Research Institute (November 1977), pages 122 to 126. Examples of particularly advantageous supported catalysts are those which contain from 20 to 40% by weight of copper, which can additionally contain small amounts of other metals, eg. chromium.

The butane-1,4-diol is isolated by distillation from the alcohol in the mixture obtained during hydrogenation. If butane-1,4-diol is used as the alcohol, isolation is unnecessary since the hydrogenolysis product of di-(4-hydroxybutyl) maleate is exclusively butane-1,4-diol. When alkanols which are higher boiling than butane-1,4-diol, eg. decan-1-ol, are used, the distillative isolation of the butane-1,4-diol from the reacted mixture is energetically more favorable than when 2-ethylhexanol, which is lower boiling than the end product, is used.

EXAMPLE 1

500 l per hour of a gaseous reaction mixture, which has been cooled to 150° C., was obtained by catalytic oxidation of a C$_4$ cut by air, and contains, per 100 l (S.T.P.), 3 g of maleic anhydride and 3.5 g of water, are passed into the bottom of a glass laboratory bubble cap column containing 8 trays. 450 ml/hour of 2-ethylhexan-1-ol are added at the top of the column, which is also at 120° C. Samples taken from the trays show that the greater part of the maleic anhydride is washed out of the gas stream, with the formation of the corresponding half-ester, at the lowest tray.

The solution, issuing from the absorption column, of the maleic acid half-ester in the excess of 2-ethylhexanol is refluxed, and the water resulting from the formation of the diester is removed from the reaction mixture by means of a separating vessel located below the reflux condenser.

The resulting solution of di-(2-ethylhexyl) maleate in 2-ethylhexan-1-ol is treated with hydrogen, in a trickle procedure, over a Cu/Mg silicate catalyst, at 190° C. and under a pressure of 200 bar, and the ester is cleaved to give butane-1,4-diol and 2-ethylhexanol. The mean space-time yield in a 3,300 hour experiment is 40 g of butanediol per liter per hour.

Under the above conditions, about 2% of the butanediol formed is converted into tetrahydrofuran. When the residence time of the reactants in the reactor is increased, the amount of tetrahydrofuran formed increases to up to 25% of the resulting butanediol. The percentage of tetrahydrofuran produced can thus be adjusted in a simple manner, within certain limits, by choosing the appropriate residence time during hydrogenation.

When the reacted mixture is worked up by distillation, tetrahydrofuran and butane-1,4-diol are obtained as pure products, and the recovered 2-ethylhexanol can be reused for absorption of maleic anhydride by this process.

The purity of the butane-1,4-diol after distillation is determined as 99.7% by weight by gas chromatographic analysis. The yield of useful products, ie. the sum of butane-1,4-diol and tetrahydrofuran, is 96% of theory. The most important by-product is butyrolactone.

EXAMPLE 2

In a laboratory apparatus corresponding to that described in Example 1, the maleic anhydride is washed out, using 250 ml/hour of butane-1,4-diol at 150° C., from a gaseous reaction mixture (500 l per hour) at 150° C., which mixture was obtained by catalytic oxidation of a $C_4$ cut by air and contains, per 100 l, 3 g of maleic anhydride and 3.5 g of water.

The resulting solution is heated to 140° C. for further esterification. The resulting water is distilled off together with the tetrahydrofuran also formed.

The solution of di-(4-hydroxybutyl) maleate in butane-1,4-diol is treated with hydrogen, over a CuO/$Cr_2O_3$ silicic acid catalyst (25% by weight of CuO and 1% by weight of $Cr_2O_3$), at 195° C. and under a pressure of 200 bar. The butane-1,4-diol obtained contains tetrahydrofuran in an amount of 5% by weight, based on butanediol formed from maleic anhydride. The purity of the butane-1,4-diol purified by distillation is 99.5% (gas chromatographic analysis).

For re-use for absorption, only some, if any, of the crude butanediol produced in the hydrogenation requires to be worked up by distillation.

EXAMPLE 3

750 l/hour of a gaseous reaction mixture at 150° C., which was obtained by catalytic oxidation of a $C_4$ cut by air, and contains, per 100 l, 3 g of maleic anhydride and 3.5 g of water, are passed into a laboratory apparatus corresponding to that used in Example 1. The reaction mixture is washed out, in counter-current, with 200 ml/hour of dodecan-1-ol at 150° C. The solution obtained is treated, as described in Example 1, for further esterification and removal of the water of reaction. The resulting solution of didodecyl maleate in the dodecanol used in excess is then treated with hydrogen at 200° C. and under a pressure of 200 bar, over an Adkins catalyst (34% by weight of Cu, 32% by weight of Cr and 10% by weight of Ba), and the ester is hydrogenolytically cleaved to give butane-1,4-diol and dodecan-1-ol.

In the subsequent distillation, tetrahydrofuran (3% by weight, based on butane-1,4-diol, purity: 99.5% by weight according to gas chromatographic analysis) and butane-1,4-diol (purity: 99.6% by weight according to gas chromatographic analysis) are obtained as top products.

A small proportion (5% by weight) of the dodecanol remaining at the bottom is freed from higher boiling impurities by distillation, but the greater part is reused, without any purification, for absorption by this process.

We claim:

1. In a process for the preparation of butane-1,4-diol by the catalytic hydrogenation of an alcoholic solution of maleic acid ester, the improvements comprising: catalytically oxidizing hydrocarbon by air to form a gaseous mixture containing maleic anhydride; washing said mixture with a monohydric or polyhydric aliphatic alcohol having a boiling point above 180° C. to form a solution of maleic acid half-ester in the alcohol; and heating the solution to remove water and to form a solution of maleic acid diester in the alcohol.

2. A process as claimed in claim 1, wherein a monohydric aliphatic alcohol of not less than 8 carbon atoms is used.

3. A process as claimed in claim 1, wherein the alcohol used has a boiling point which is not less than 10° C. higher than the boiling point of butane-1,4-diol.

4. A process as claimed in claim 1, wherein 2-ethylhexanol or dodecan-1-ol is used as the alcohol.

* * * * *